United States Patent
Koseoglu et al.

(10) Patent No.: US 9,816,919 B2
(45) Date of Patent: Nov. 14, 2017

(54) CHARACTERIZATION OF CRUDE OIL BY SIMULATED DISTILLATION

(75) Inventors: Omer Refa Koseoglu, Dhahran (SA); Adnan Al-Hajji, Dammam (SA); Frederick Marie Adam, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 450 days.

(21) Appl. No.: 13/397,312

(22) Filed: Feb. 15, 2012

(65) Prior Publication Data

US 2015/0106032 A1 Apr. 16, 2015

(51) Int. Cl.
 G06F 7/60 (2006.01)
 G06F 17/10 (2006.01)
 G01N 21/33 (2006.01)
 G01N 33/28 (2006.01)

(52) U.S. Cl.
 CPC .......... *G01N 21/33* (2013.01); *G01N 33/2823* (2013.01); *G01N 2201/129* (2013.01)

(58) Field of Classification Search
 USPC .................................................. 703/2, 9, 10
 See application file for complete search history.

(56) References Cited

U.S. PATENT DOCUMENTS

| 4,971,915 A | 11/1990 | Schwartz |
| 2007/0050154 A1* | 3/2007 | Albahri ................. G01N 25/14 702/22 |

FOREIGN PATENT DOCUMENTS

| WO | 20040033513 A2 | 4/2004 |
| WO | 20130102916 A1 | 7/2013 |

OTHER PUBLICATIONS

James Speight "Handbook of Petroleum Product Analysis" 2002.*
Anonymous: "ASTM D2887-01 Standard Test Method for Boiling Range Distribution of Petroleum Fractions by Gas Chromatography," May 2001 (13 pages).

* cited by examiner

*Primary Examiner* — Saif Alhija
(74) *Attorney, Agent, or Firm* — Abelman, Frayne & Schwab

(57) ABSTRACT

A system and a method for calculating the cetane number, pour point, cloud point and aniline point of gas oil fractions of a crude oil sample from the density and gas chromatographic simulated distribution of the sample.

12 Claims, 3 Drawing Sheets

CHARACTERIZATION OF CRUDE OIL BY SIMULATED DISTILLATION

RELATED APPLICATION

This application claims the benefit of U.S. Provisional Patent Application No. 61/445,183 filed Feb. 22, 2011, the disclosure of which is hereby incorporated by reference.

FIELD OF THE INVENTION

This invention relates to a method and process for the evaluation of samples of crude oil and its fractions by simulated distillation (SD), avoiding the need to conduct fractionation/distillation assays.

BACKGROUND OF THE INVENTION

Crude oil originates from the decomposition and transformation of aquatic, mainly marine, living organisms and/or land plants that became buried under successive layers of mud and silt some 15-500 million years ago. They are essentially very complex mixtures of many thousands of different hydrocarbons. Depending on the source, the oil predominantly contains various proportions of straight and branched-chain paraffins, cycloparaffins, and naphthenic, aromatic, and polynuclear aromatic hydrocarbons. These hydrocarbons can be gaseous, liquid, or solid under normal conditions of temperature and pressure, depending on the number and arrangement of carbon atoms in the molecules.

Crude oils vary widely in their physical and chemical properties from one geographical region to another and from field to field. Crude oils are usually classified into three groups according to the nature of the hydrocarbons they contain: paraffinic, naphthenic, asphaltic, and their mixtures. The differences are due to the different proportions of the various molecular types and sizes. One crude oil can contain mostly paraffins, another mostly naphthenes. Whether paraffinic or naphthenic, one can contain a large quantity of lighter hydrocarbons and be mobile or contain dissolved gases; another can consist mainly of heavier hydrocarbons and be highly viscous, with little or no dissolved gas. Crude oils can also include heteroatoms containing sulfur, nitrogen, nickel, vanadium and others elements in quantities that impact the refinery processing of the crude oil fractions. Light crude oils or condensates can contain sulfur in concentrations as low as 0.01 W % of sulfur; in contrast, heavy crude oils can contain as much as 5-6 W %. Similarly, the nitrogen content of crude oils can range from 0.001-1.0 W %.

The nature of the crude oil governs, to a certain extent, the nature of the products that can be manufactured from it and their suitability for special applications. A naphthenic crude oil will be more suitable for the production of asphaltic bitumen, a paraffinic crude oil for wax. A naphthenic crude oil, and even more so an aromatic one, will yield lubricating oils with viscosities that are sensitive to temperature. However, with modern refining methods there is greater flexibility in the use of various crude oils to produce many desired type of products.

A crude oil assay is a traditional method of determining the nature of crude oils for benchmarking purposes. Crude oils are subjected to true boiling point (TBP) distillations and fractionations to provide different boiling point fractions. The crude oil distillations are carried out using the American Standard Testing Association (ASTM) Method D 2892. The common fractions and their nominal boiling points are given in Table 1.

TABLE 1

| Fraction | Boiling Point, ° C. |
| --- | --- |
| Methane | −161.5 |
| Ethane | −88.6 |
| Propane | −42.1 |
| Butanes | −6.0 |
| Light Naphtha | 36-90 |
| Mid Naphtha | 90-160 |
| Heavy Naphtha | 160-205 |
| Light gas Oil | 205-260 |
| Mid Gas Oil | 260-315 |
| Heavy gas Oil | 315-370 |
| Light Vacuum Gas Oil | 370-430 |
| Mid Vacuum Gas Oil | 430-480 |
| Heavy vacuum gas oil | 480-565 |
| Vacuum Residue | 565+ |

The yields, composition, physical and indicative properties of these crude oil fractions, where applicable, are then determined during the crude assay work-up calculations. Typical compositional and property information obtained from a crude oil assay is given in Table 2.

TABLE 2

| Property | Unit | Property Type | Fraction |
| --- | --- | --- | --- |
| Yield Weight and Volume % | W % | Yield | All |
| API Gravity | ° | Physical | All |
| Viscosity Kinematic @ 38° C. | ° | Physical | Fraction boiling >250° C. |
| Refractive Index @ 20° C. | Unitless | Physical | Fraction boiling <400° C. |
| Sulfur | W % | Composition | All |
| Mercaptan Sulfur, W % | W % | Composition | Fraction boiling <250° C. |
| Nickel | ppmw | Composition | Fraction boiling >400° C. |
| Nitrogen | ppmw | Composition | All |
| Flash Point, COC | ° C. | Indicative | All |
| Cloud Point | ° C. | Indicative | Fraction boiling >250° C. |
| Pour Point, (Upper) | ° C. | Indicative | Fraction boiling >250° C. |
| Freezing Point | ° C. | Indicative | Fraction boiling >250° C. |
| Microcarbon Residue | W % | Indicative | Fraction boiling >300° C. |
| Smoke Point, mm | mm | Indicative | Fraction boiling between 150-250 |
| Cetane Index | Unitless | Indicative | Fraction boiling between 150-400 |
| Aniline Point | ° C. | Indicative | Fraction boiling <520° C. |

Due to the number of distillation cuts and the number of analyses involved, the crude oil assay work-up is both costly and time consuming.

In a typical refinery, crude oil is first fractionated in the atmospheric distillation column to separate sour gas and light hydrocarbons, including methane, ethane, propane, butanes and hydrogen sulfide, naphtha (36°-180° C.), kerosene (180°-240° C.), gas oil (240°-370° C.) and atmospheric residue (>370° C.). The atmospheric residue from the atmospheric distillation column is either used as fuel oil or sent to a vacuum distillation unit, depending on the configuration of the refinery. The principal products obtained from vacuum distillation are vacuum gas oil, comprising hydrocarbons boiling in the range 370°-520° C., and vacuum residue, comprising hydrocarbons boiling above 520° C. The crude assay data help refiners to understand the general composition of the crude oil fractions and properties so that the fractions can be processed most efficiently and effectively in an appropriate refining unit. Indicative properties are used to determine the engine/fuel performance or usability or flow characteristic or composition. A summary of the indicative properties and determination methods with description are given below.

The cetane number of diesel fuel oil, determined by the ASTM D613 method, provides a measure of the ignition quality of diesel fuel; as determined in a standard single cylinder test engine; which measures ignition delay compared to primary reference fuels. The higher the cetane number; the easier the high-speed; direct-injection engine will start; and the less white smoking and diesel knock after start-up are. The cetane number of a diesel fuel oil is determined by comparing its combustion characteristics in a test engine with those for blends of reference fuels of known cetane number under standard operating conditions. This is accomplished using the bracketing hand wheel procedure which varies the compression ratio (hand wheel reading) for the sample and each of the two bracketing reference fuels to obtain a specific ignition delay, thus permitting interpolation of cetane number in terms of hand wheel reading.

The cloud point, determined by the ASTM D2500 method, is the temperature at which a cloud of wax crystals appears when a lubricant or distillate fuel is cooled under standard conditions. Cloud point indicates the tendency of the material to plug filters or small orifices under cold weather conditions. The specimen is cooled at a specified rate and examined periodically. The temperature at which cloud is first observed at the bottom of the test jar is recorded as the cloud point. This test method covers only petroleum products and biodiesel fuels that are transparent in 40 mm thick layers, and with a cloud point below 49° C.

The pour point of petroleum products, determined by the ASTM D97 method, is an indicator of the ability of oil or distillate fuel to flow at cold operating temperatures. It is the lowest temperature at which the fluid will flow when cooled under prescribed conditions. After preliminary heating, the sample is cooled at a specified rate and examined at intervals of 3° C. for flow characteristics. The lowest temperature at which movement of the specimen is observed is recorded as the pour point.

The aniline point, determined by the ASTM D611 method, is the lowest temperature at which equal volumes of aniline and hydrocarbon fuel or lubricant base stock are completely miscible. A measure of the aromatic content of a hydrocarbon blend is used to predict the solvency of a base stock or the cetane number of a distillate fuel Specified volumes of aniline and sample, or aniline and sample plus n-heptane, are placed in a tube and mixed mechanically. The mixture is heated at a controlled rate until the two phases become miscible. The mixture is then cooled at a controlled rate and the temperature at which two phases separate is recorded as the aniline point or mixed aniline point.

To determine these properties of gas oil or naphtha fractions conventionally, these fractions have to be distilled off from the crude oil and then measured/determined using various analytical methods that are laborious, costly and time consuming.

SD is a technique which separates individual hydrocarbon components in the order of their boiling points, and is used to simulate time-consuming laboratory-scale physical distillation procedures. The separation is usually accomplished with a gas chromatograph equipped with a chromatography column coated with a nonpolar (hydrocarbon-like) stationary phase, an oven and injector which can be temperature programmed with. A flame ionization detector (FID) is used for detection and measurement of the hydrocarbon analytes. The SD analysis result provides a quantitative percent mass yield as a function of boiling point of the hydrocarbon components of the sample being analyzed. The chromatographic elution times of the hydrocarbon components are calibrated to the atmospheric equivalent boiling point (AEBP) of the individual n-alkane as described in a method from the ASTM by using n-alkane (n-paraffin) reference material. In the SD method ASTM D2887, the n-alkane calibration reference covers the boiling range 55-538° C. (100-1000° F.) which covers the n-alkanes with a chain length of about C5-C44.

Alternative methods may be used, including ASTM D5236, ASTM D86, ASTM D5399, ASTM D6352-04, ASTM D7213-05e1, ASTM D7398-07, ASTM D7169-05, ASTM D7096-10, ASTM D7500-10, ASTM D5307-97, ASTM D1160, ASTM D2892, or any other methods based upon gas chromatography, true boiling point distillation, supercritical fluid chromatography, and equilibrium flash. There are well-known correlations to convert distillation numbers: for example, if the true boiling point distillation (ASTM D2892) is known, the SD data (ASTM D2892) can be estimated. While there are not yet ASTM methods using supercritical fluid chromatography, non-standardized lab methods are known.

In the high temperature simulated distillation method (HTSD), the n-alkane calibration reference (a hydrogenated polyolefin wax, polywax 655) covers the boiling range 36-750° C. (97-1382° F.) which covers the n-alkanes with a chain length of about C5-C120. A key difference between ASTM D2887 and HTSD is the ability of HTSD to handle residue-containing samples (i.e. material boiling>538° C. or 1000° F.). SD and laboratory-scale physical distillation methods are routinely used for determining boiling ranges of petroleum crude oils and refined products. The boiling points with yield profile data of these materials are used by refinery engineers to make operational decisions to improve product yields and product quality. SD is valuable for, and can improve results from, computer modeling of refining processes for improvements in design and process optimization. Precise yield correlations between HTSD and crude assay distillation (a procedure which uses methods ASTM D2892 and D5236) have allowed HTSD to be successfully used in place of the physical distillation procedures. A typical simulated distillation chart obtained from a gas chromatogram of crude oil is shown in FIG. 1, where the W % of distilled fractions is plotted against the boiling temperature.

Any new rapid, direct method to help better understand the crude oil composition and properties from the analysis of whole crude oil will save producers, marketers, refiners and/or other crude oil users substantial expense, effort and time. Therefore, a need exists for an improved system and method for determining the properties of crude fractions from different sources and classifying the crude oil fractions based on their boiling point characteristics and/or properties.

SUMMARY OF THE INVENTION

The above objects and further advantages are provided by the present invention which broadly comprehends a system and a method for determining the indicative properties of a hydrocarbon sample. In accordance with the invention, indicative properties (i.e., cetane number, pour point, cloud point and aniline point) of gas oil fraction in crude oils are predicted by density and simulated distillation of crude oils. The correlations also provide information about the gas oil properties without fractionation/distillation (crude oil assays) and will help producers, refiners, and marketers to benchmark the oil quality and, as a result, valuate the oils without performing the customary extensive and time-consuming crude oil assays.

BRIEF DESCRIPTION OF THE DRAWINGS

Further advantages and features of the present invention will become apparent from the following detailed description of the invention when considered with reference to the accompanying drawings, in which.

DETAILED DESCRIPTION OF INVENTION

Crude oils' simulated distillation were obtained by gas chromatography according to the ASTM Method 5236 and/or its derivation for high temperature.

Figure 1:
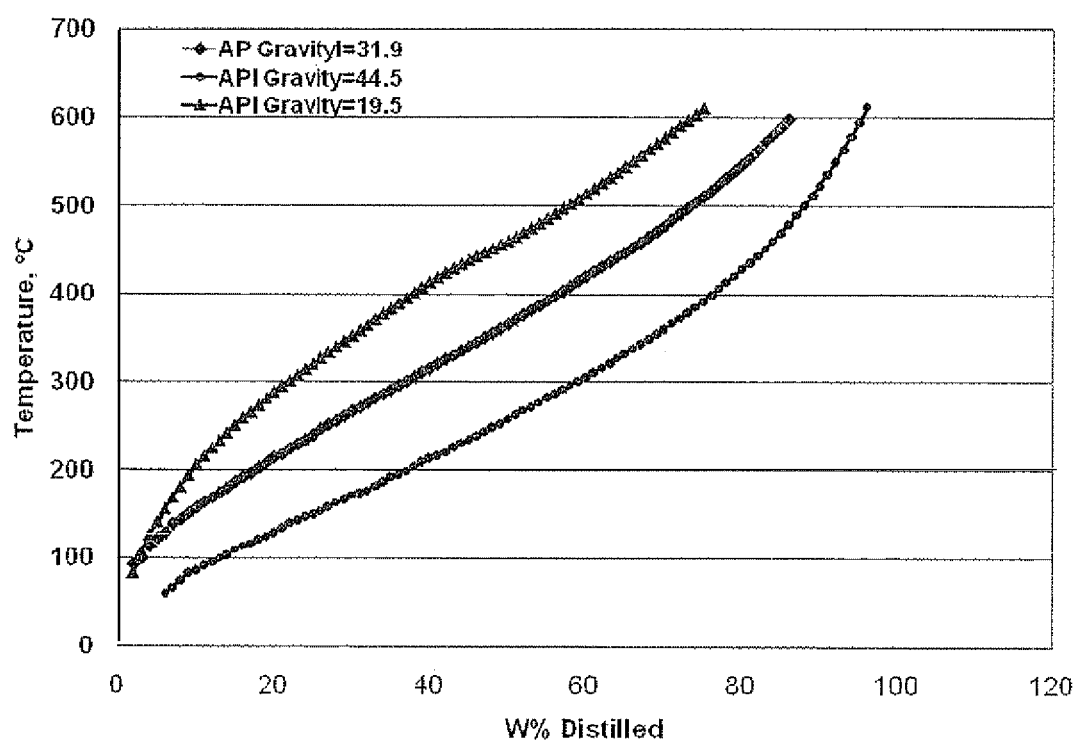
FIG. 1 is a graphic plot of simulated distillation data obtained from gas chromatography for three types of crude oil.
Figure 2:
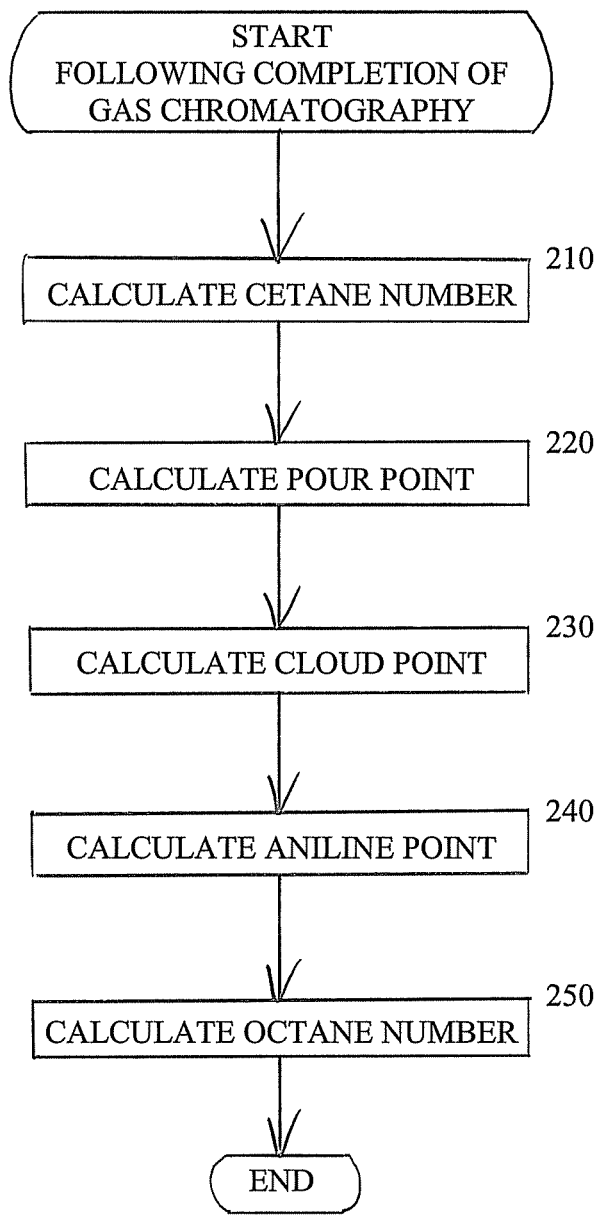
FIG. 2 is a process flow diagram of steps carried out to establish a value for indicative properties of a gas oil fraction, using the system and method of the present invention.

The indicative properties (i.e., the cetane number, pour point, cloud point and aniline point) of the gas oil fraction boiling in the range 180-370° C. can be predicted from the density (at 15° C./4° C.) and the mid boiling point of the gas oil or whole crude oil ($T_{MBP}$), measured in Kelvin. FIG. 2 shows a process flowchart of steps that occur after gas chromatography is completed and the results are tabulated. In step 210, the cetane number is calculated. In step 220, the pour point is calculated. In step 230, the cloud point is calculated. In step 240, the aniline point is calculated. In step 250, the octane number is calculated. While FIG. 2 shows the steps performed sequentially, they can be performed in any order.

That is, $$\text{Indicative Property} = f(\text{density}(15/4)_{crude\ oil}, T_{MBP}(K))_{gas\ oil} \quad (1a);$$

$$\text{Indicative Property} = f(\text{density}(15/4)_{crude\ oil}, T_{MBP}(K))_{crude\ oil} \quad (1b);$$

Equations (2) through (5) show, respectively, the cetane number, pour point, cloud point and aniline point that can be predicted from the density and simulated distillation of crude oils.

$$\begin{aligned}\text{Cetane Number (CET)} &= K_{CET} + X1_{CET}*\text{DEN} + X2_{CET}*\text{DEN}^2 + X3_{CET}*\text{DEN}^3 + X4_{CET}*(T_{MBP}/1000) \\ &+ X5_{CET}*(T_{MBP}/1000)^2 + X6_{CET}*(T_{MBP}/1000)^3 + X7_{CET}*\text{DEN}*(T_{MBP}/1000)\end{aligned} \quad (2);$$

$$\begin{aligned}\text{Pour Point (PP)} &= K_{PP} + X1_{PP}*\text{DEN} + X2_{PP}*\text{DEN}^2 + X3_{PP}*\text{DEN}^3 + X4_{PP}*(T_{MBP}/1000) \\ &+ X5_{PP}*(T_{MBP}/1000) + X6_{PP}*(T_{MBP}/1000)^3 + X7_{PP}*\text{DEN}*(T_{MBP}/1000)\end{aligned} \quad (3);$$

$$\begin{aligned}\text{Cloud Point (CP)} &= K_{CP} + X1_{CP}*\text{DEN} + X2_{CP}*\text{DEN}^2 + X3_{CP}*\text{DEN}^3 + X4_{CP}*(T_{MBP}/1000) + X5_{CP}*(T_{MBP}/1000) \\ &+ X6_{CP}*(T_{MBP}/1000)^3 + X7_{CP}*\text{DEN}*(T_{MBP}/1000)\end{aligned} \quad (4);$$

$$\begin{aligned}\text{Aniline Point (AP)} &= K_{AP} + X1_{AP}*\text{DEN} + X2*\text{DEN}^2 + X3_{AP}*\text{DEN}^3 + X4_{AP}*(T_{MBP}/1000) + X5_{AP}*(T_{MBP}/1000)^2 \\ &+ X6_{AP}*(T_{MBP}/1000)^3 + X7_{AP}*\text{DEN}*(T_{MBP}/1000)\end{aligned} \quad (5);$$

where:

DEN=density of the crude oil sample;

$T_{MBP}$=mid boiling point of the gas oil or crude oil (derived from the simulated distillation curves of crude oils);

and $K_{CET}$, $X1_{CET}$-$X7_{CET}$, $K_{PP}$, $X1_{PP}$-$X7_{PP}$, $K_{CP}$, $X1_{CP}$-$X7_{CP}$, $K_{AP}$, and $X1_{AP}$-$X7_{AP}$ are constants that were developed using linear regression techniques, and which are given in Table 3.

TABLE 3

| Property | Cetane Number (CET) | Pour Point (PP) | Cloud Point (CP) | Aniline Point (AP) |
|---|---|---|---|---|
| K | 544509.8 | 1344488.4 | 395024.0 | 24390.7 |
| X1 | −1932359.8 | −4907366.2 | −1429569.6 | −49357.1 |
| X2 | 2161099.3 | 5503008.0 | 1604628.0 | 52455.3 |
| X3 | −796440.7 | −2031119.7 | −592968.1 | −18616.3 |
| X4 | 142762.7 | 527938.4 | 136360.5 | −41985.4 |
| X5 | −177339.2 | −699945.0 | −177392.5 | 65171.0 |
| X6 | 90209.8 | 361176.8 | 91570.3 | −33881.4 |
| X7 | −30458.6 | −87436.2 | −25137.2 | 408.8 |

Note that as an alternative to determining the mid boiling point of the oil stream at the 50 W % point of the simulated distillation data, it may be calculated by taking the average of boiling points. Alternatively, it may be calculated as a weighted average boiling point (WABP), as shown in equation (6), below.

$$WABP = \frac{(T_{10}*10) + (T_{30}*30) + (T_{50}*50) + (T_{70}*70) + T_{90}*90)}{10+30+50+70+90}, \quad (6)$$

where $T_{10}$ is the boiling temperature of oil determined when 10 W % or V % of the fraction is recovered during the distillation, and where $T_{30}$, $T_{50}$, $T_{70}$ and $T_{90}$ are determined accordingly. An example calculation of WABP is presented below. When the sample is distilled, the boiling point of the sample is determined to be 149° C. when 10 W % of the sample is recovered. Thus, $T_{10}$ is 149° C., and the other figures are determined similarly:

| | W % Recovered | | | | |
|---|---|---|---|---|---|
| | 10 | 30 | 50 | 70 | 90 |
| Boiling Temperature, °C. | 149 | 230 | 282 | 325 | 371 |

$$WABT = [149*10 + 230*30 + 282*50 + 325*70 + 371*90] /$$
$$[10 + 30 + 50 + 70 + 90] = 315$$

The following example is provided to demonstrate an application of equations (2) through (5). A sample of Arabian medium crude with a 15° C./4° C. density of 0.8828 Kg/l was analyzed by gas chromatography using the ASTM D2887 method. The simulated distillation data is shown in Table 4:

TABLE 4

| W % | Temp. °C. |
|---|---|
| 0 | |
| 1 | |
| 2 | 37 |
| 3 | 68 |
| 4 | 83 |
| 5 | 94 |
| 6 | 100 |
| 7 | 113 |
| 8 | 121 |
| 9 | 127 |
| 10 | 138 |
| 11 | 144 |
| 12 | 151 |
| 13 | 157 |
| 14 | 165 |
| 15 | 172 |
| 16 | 175 |
| 17 | 185 |
| 18 | 191 |
| 19 | 196 |
| 20 | 204 |
| 21 | 210 |
| 22 | 216 |
| 23 | 222 |
| 24 | 229 |
| 25 | 235 |
| 26 | 241 |
| 27 | 249 |
| 28 | 255 |
| 29 | 261 |
| 30 | 267 |
| 31 | 272 |
| 32 | 279 |
| 33 | 285 |
| 34 | 290 |
| 35 | 297 |
| 36 | 303 |
| 37 | 308 |
| 38 | 315 |
| 39 | 319 |
| 40 | 326 |
| 41 | 331 |
| 42 | 337 |
| 43 | 342 |
| 44 | 348 |
| 45 | 354 |
| 46 | 360 |
| 47 | 366 |
| 48 | 372 |
| 49 | 378 |
| 50 | 384 |
| 51 | 390 |
| 52 | 396 |
| 53 | 402 |
| 54 | 409 |
| 55 | 415 |
| 56 | 422 |
| 57 | 428 |
| 58 | 434 |
| 59 | 440 |
| 60 | 446 |
| 61 | 452 |
| 62 | 458 |
| 63 | 465 |
| 64 | 471 |
| 65 | 478 |
| 66 | 485 |
| 67 | 492 |
| 68 | 499 |
| 69 | 506 |
| 70 | 513 |
| 71 | 520 |
| 72 | 528 |
| 73 | 535 |
| 74 | 543 |
| 75 | 551 |
| 76 | 559 |
| 77 | 567 |
| 78 | 575 |
| 79 | 583 |
| 80 | 592 |
| 81 | 599 |
| 82 | 608 |

The mid boiling point of the crude oil is taken from the data at the 50 W % point, which is 384° C. (657 K).

Applying equation 2 and the constants from Table 3, $$\text{Cetane Number}(CET) = $$
$$K_{CET} + X1_{CET}*DEN + X2_{CET}*DEN^2 + X3_{CET}*DEN^3 + $$
$$X4_{CET}*(T_{MBP}/1000) + X5_{CET}*(T_{MBP}/1000)^2 + $$
$$X6_{CET}*T(T_{MBP}/1000)^3 + X7_{CET}*DEN*(T_{MBP}/1000) = $$
$$(544509.8) + (-1932359.8)(0.8828) + (2161099.3)(0.8828)^2 + $$
$$(-796440.7)(0.8828)^3 + (142762.7)(657/1000) + $$
$$(-177339.2)(657/1000)^2 + (90209.8)(657/1000)^3 + $$
$$(-30458.6)(0.8828)(657/1000) = 59$$

Applying equation 3 and the constants from Table 3, $$\text{Pour Point}(PP) = K_{PP} + X1_{PP}*DEN + X2_{PP}*DEN^2 + $$
$$X3_{PP}*DEN^3 + X4_{PP}*(T_{MBP}/1000) + X5_{PP}*(T_{MBP}/1000)^2 + $$
$$X6_{PP}*(T_{MBP}/1000)^3 + X7_{PP}*DEN*(T_{MBP}/1000) = $$
$$(1344488.4) + (-4907366.2)(0.8828) + (5503008.06)(0.8828)^2 + $$
$$(-2031119.7)(0.8828)^3 + (527938.4)(657/1000) + $$
$$(-699945.0)(657/1000)^2 + (361176.8)(657/1000)^3 + $$
$$(-87436.2)(0.8828)(657/1000) = -10$$

Applying equation 4 and the constants from Table 3, $$\text{Cloud Point}(CP) = K_{CP} + X1_{CP}*DEN + X2_{CP}*DEN^2 + $$
$$X3_{CP}*DEN^3 + X4_{CP}*(T_{MBP}/1000) + X5_{CP}*(T_{MBP}/1000)^2 + $$
$$X6_{CP}*(T_{MBP}/1000)^3 + X7_{CP}*DEN*(T_{MBP}/1000) = $$

-continued
$$(39502.0) + (-1429569.6)(0.8828) + (1604628.0)(0.8828)^2 +$$
$$(-592968.1)(0.8828)^3 + (136360.5)(657/1000) +$$
$$(-177392.5)(657/1000)^2 + (91570.3)(657/1000)^3 +$$
$$(-25137.2)(0.8828)(657/1000) = -10$$

Applying equation 5 and the constants from Table 3, $$\text{Aniline Point } (AP) =$$
$$K_{AP} + X1_{AP}*DEN + X2_{AP}*DEN^2 + X3_{AP}*DEN^3 +$$
$$X4_{AP}*(T_{MBP}/1000) + X5_{AP}*(T_{MBP}/1000)^2 +$$
$$X6_{AP}*(T_{MBP}/1000)^3 + X7_{AP}*DEN*(T_{MBP}/1000) =$$
$$(24390.7) + (-49357.1)(0.8828) + (52455.3)(0.8828)^2 + (-18616.3)$$
$$(0.8828)^3 + (-41985.4)(657/1000) + (65171.0)(657/1000)^2 +$$
$$(-33881.4)(657/1000)^3 + (408.8)(0.8828)(657/1000) = 66$$

The method is applicable for naturally occurring hydrocarbons derived from crude oils, bitumens, heavy oils, shale oils and from refinery process units including hydrotreating, hydroprocessing, fluid catalytic cracking, coking, and visbreaking or coal liquefaction.

Figure 3:
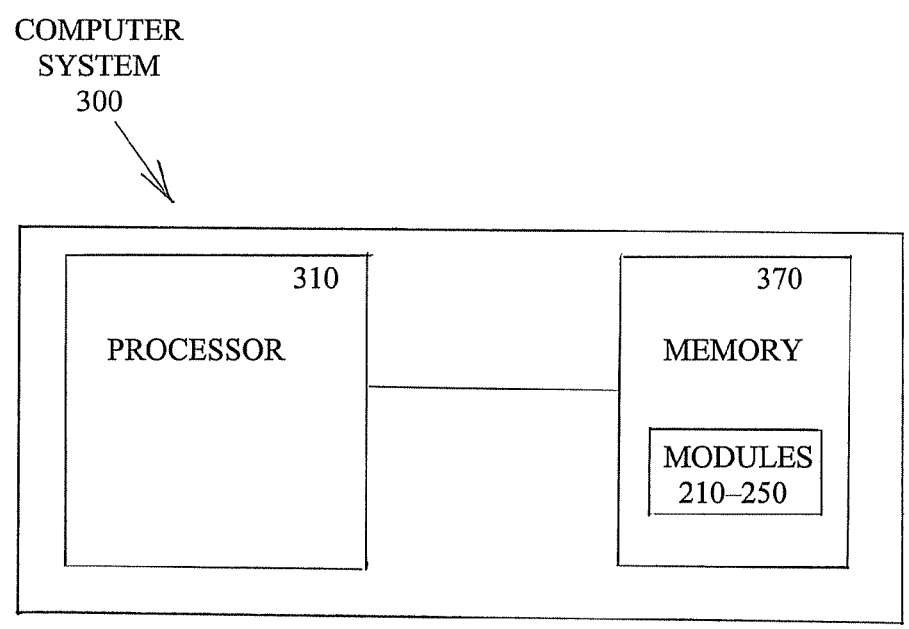
FIG. 3 is a block diagram of a component of a system for implementing the invention, according to one preferred embodiment of the present invention.

FIG. 3 illustrates one embodiment of the present invention, implemented in a computer system 300, with a number of modules. Computer system 300 includes a processor 310, and a memory unit 370. Memory unit 370 stores software program modules and associated data, and in particular stores a cetane number calculation module 210, a pour point calculation module 220, a cloud point calculation module 230, an aniline point calculation module 240, and an octane number calculation module 250.

The system and method of the present invention have been described above and with reference to the attached figure; however, modifications will be apparent to those of ordinary skill in the art and the scope of protection for the invention is to be defined by the claims that follow.

We claim:

1. A system for evaluating a crude oil sample and calculating indicative properties of a gas oil fraction of the crude oil without first distilling the gas oil fraction, the system comprising:
   a gas chromatograph;
   a non-volatile memory device that stores calculation modules and data;
   a processor coupled to the non-volatile memory;
   a first calculation module that calculates a mid boiling point of the crude oil sample from simulated distillation data obtained from the gas chromatograph;
   a second calculation module that calculates as one of the indicative properties the cetane number for the gas oil fraction of the crude oil from a two-variable polynomial equation with a first set of predetermined constant coefficients developed using linear regression techniques;
   a third calculation module that calculates as one of the indicative properties the pour point for the gas oil fraction of the crude oil from the two-variable polynomial equation with a second set of predetermined constant coefficients developed using linear regression techniques;
   a fourth calculation module that calculates as one of the indicative properties the cloud point for the gas oil fraction of the crude oil from the two-variable polynomial equation with a third set of predetermined constant coefficients developed using linear regression techniques; and
   a fifth calculation module that calculates as one of the indicative properties the aniline point for the gas oil fraction of the crude oil from the two-variable polynomial equation with a fourth set of predetermined constant coefficients developed using linear regression techniques;
   a sixth calculation module that determines from the indicative properties the nature of products that can be manufactured from the crude oil; and
   a seventh calculation module that determines an appropriate refining technology to allow the gasoline and gas oil fractions to be processed most efficiently and effectively;
   wherein the two variables of the two-variable polynomial equation are the mid boiling point and the density of the crude oil sample.

2. A method for evaluating a crude oil sample to calculate indicative properties of a gas oil fraction of the crude oil without first distilling the gas oil fraction, the method comprising:
   subjecting said crude oil sample to gas chromatographic simulated distillation (SD) analysis;
   obtaining the density of the crude oil sample;
   calculating a mid boiling point of the crude oil sample from SD data obtained from the gas chromatographic SD analysis;
   calculating as one of the indicative properties the cetane number for the gas oil fraction from a two-variable polynomial equation with a first set of predetermined constant coefficients developed using linear regression techniques;
   calculating as one of the indicative properties the pour point for the gas oil fraction from the two-variable polynomial equation with a second set of predetermined constant coefficients developed using linear regression techniques;
   calculating as one of the indicative properties the cloud point for the gas oil fraction from the two-variable polynomial equation with a third set of predetermined constant coefficients developed using linear regression techniques;
   calculating as one of the indicative properties the aniline point for the gas oil fraction from the two-variable polynomial equation with a fourth set of predetermined constant coefficients developed using linear regression techniques;
   determining from the indicative properties the nature of products that can be manufactured from the crude oil; and
   determining an appropriate refining technology to allow the gasoline and gas oil fractions to be processed most efficiently and effectively,
   wherein the two variables of the two-variable polynomial equation are the mid boiling point and the density of the crude oil sample.

3. The method of claim 2, wherein the SD data is obtained from gas chromatography methods including ASTM D2887, ASTM D5236, ASTM D5399, ASTM D6352-04, ASTM D7213-05e1, ASTM D7398-07, ASTM D7169-05, ASTM D7096-10, ASTM D7500-10, and ASTM D5307-97.

4. The method of claim 2, wherein the SD data is obtained from supercritical fluid chromatography methods.

5. The method of claim 2, wherein the mid-boiling point is the mid-boiling point of whole crude oil.

6. The method of claim 2, wherein the mid-boiling point of the crude oil is calculated at the 50 W % point of the SD data.

7. The method of claim 2, wherein the mid-boiling point of the crude oil is calculated by taking the average of boiling points.

8. The method of claim 2, wherein the mid-boiling point of the crude oil is calculated by taking the weighted average of boiling points.

9. The method of claim 2, wherein correlative SD data is obtained from distillation methods selected from the group composed of ASTM D86, ASTM D1160, ASTM D2892, or any other methods based upon true boiling point distillation, supercritical fluid chromatography, and equilibrium flash.

10. The method of claim 9, wherein the true boiling point distillations were conducted in a column with a number of theoretical trays in the range 0-100.

11. The method of claim 9, wherein the true boiling point distillations were conducted in a column with a number of theoretical trays in the range 10-30.

12. The method of claim 9, wherein the true boiling point distillations were conducted in a column with a number of theoretical trays in the range 15-20.

* * * * *